United States Patent [19]
Joseph et al.

[11] Patent Number: 5,169,599
[45] Date of Patent: Dec. 8, 1992

[54] METHOD AND APPARATUS FOR OPTICALLY DETECTING PRESENCE OF IMMUNOLOGICAL COMPONENTS

[75] Inventors: Jose P. Joseph, Menlo Park, Calif.; Kiminori Itoh, Tokyo, Japan

[73] Assignee: Teknekron Sensor Development Corporation, Menlo Park, Calif.

[21] Appl. No.: 576,359

[22] Filed: Aug. 30, 1990

[51] Int. Cl.$^5$ .................. G01N 31/22; G01N 33/553
[52] U.S. Cl. ...................................... 422/57; 436/525; 436/808; 436/810
[58] Field of Search ............... 422/57; 436/525, 808, 436/810

[56] References Cited

U.S. PATENT DOCUMENTS

| | | | |
|---|---|---|---|
| 2,351,644 | 6/1944 | Talley et al. | 422/57 X |
| 3,853,467 | 12/1974 | Giaever | 422/57 X |
| 4,810,470 | 3/1989 | Burkhardt et al. | 422/57 X |
| 4,820,649 | 4/1989 | Kawaguchi et al. | 422/57 X |
| 5,063,081 | 11/1991 | Cozzette et al. | 427/2 |

OTHER PUBLICATIONS

Biostar promotional materials, J. Hanlin, "Thin Films," Photonics Spectra (Feb. 1988) pp. 113–118.

Primary Examiner—Jill A. Johnston
Attorney, Agent, or Firm—Limbach & Limbach

[57] ABSTRACT

An optical immunosensing device for detecting the presence of an analyte in a liquid sample is fabricated by coating iron phosphate onto a silicon substrate and then etching the iron phosphate layer to obtain steps of varying thickness. Then, a first mip, capable of immunological reaction with the analyte, is immobilized on the iron phosphate steps. In the preferred embodiment, the first mip is chemically bound to the iron phosphate step surface. The presence of the analyte in the liquid sample is detected by visually observing color changes in the steps after contact of the detection zone with the liquid sample. A change in step color is related to increased thickness which can only result from the binding of the analyte to the first mip immobilized on the iron phosphate step. Aluminum phosphate can also be added to the iron phosphate.

11 Claims, 1 Drawing Sheet

METHOD AND APPARATUS FOR OPTICALLY DETECTING PRESENCE OF IMMUNOLOGICAL COMPONENTS

TECHNICAL FIELD

This invention relates generally to the optical detection of the presence of antibodies and antigens in liquid samples, and more particularly, to the use of a visible color change brought about by increasing thickness of layers coated upon a substrate as an indication of the presence of the target analyte.

BACKGROUND OF THE INVENTION

The rapid and accurate detection of extremely low concentrations of antigens and antibodies in liquid samples has been recognized as a valuable tool in the diagnosis and treatment of disease and in substance detection for safety, law enforcement, therapy and environmental applications. The development of recombinant DNA and hybridoma techniques has vastly increased the number of antibodies, antigens and haptens which can be detected by immunologically specific reactions and has improved the sensitivity of these detection methods. Previous investigators have worked with competitive assays which utilize radiation (RIA) and fluorescence to qualitatively and quantitatively signal the presence of the analyte (i.e., the substance to be detected). These techniques require expensive reagents and elaborate instrument schemes to detect and measure a signal related to the presence and amount of the target analyte.

The monoclonal antibody sandwich assay technique has also evolved as a quick and accurate method to detect immunological analytes. In the widely used ELISA, an enzyme (rather than radioactive or fluorescent) tagged component has been used to form a tagged antibody sandwich, which upon addition to the enzyme substrate generates a visually detectable calorimetric signal. One drawback of the ELISA technique is that a relatively expensive reagent (enzyme-tagged immunological component) must be used to complete the sandwich.

One analyte detection technique which does not require tagged molecules in order to generate a measurable signal related to the presence and amount of analyte present involves the use of an ellipsometer to detect changes in refractive properties on a flat reflecting surface. These surface refractive property changes occur when a liquid phase antibody/antigen binds to a solid phase antigen/antibody preadsorbed on the flat reflecting surface. The drawback of this technique, (Rothen, A., Helv. Chim. Acta, 33 834 (1950)), is that the ellipsometer is a complex and expensive instrument, making the use of this technique costly.

BioStar (Colorado) has recently developed an "interference slide" technology for detecting immunological analytes in liquid samples. This technique utilizes visual properties of interference, and anti-reflective coatings, to create altered light responses for thickness changes indicative of the target analyte.

The present invention provides an optical immunosensor which is more sensitive than the BioStar device, and which can be used to measure the amount of analyte present in a liquid sample qualitatively, semi-quantitatively, or quantitatively.

It is therefore one object of the present invention to provide films and substrates which are selected to yield distinctly different colors under assay conditions.

It is another object of the present invention to provide an optical immunosensor device fabrication method which is easy and inexpensive.

It is a further object of this invention to provide an optical immunosensor device which can be used to make qualitative, semi-quantitative and quantitative determinations of the analyte present, based upon the color changes resulting from thickness changes and upon comparisons of these colors to known standards.

These and further objects of the present invention will become apparent to the ordinary artisan by reference to the following specifications and drawings.

SUMMARY OF THE INVENTION

According to a preferred embodiment of the present invention, an optical immunosensing device comprises a silicon substrate onto which has been coated a layer of iron phosphate, and optionally aluminum phosphate, silicon dioxide or mixtures thereof. The metal-containing layer is then carefully etched with an etching acid such as phosphoric acid to obtain a plurality of steps, or regions of varying metal-containing layer coating thickness. One member of an immunological pair (mip) is then immobilized upon the metal-containing layer step surfaces, either directly or through the use of reagents which functionalize the surface to permit covalent binding of the proteins to the solid surface. In the preferred embodiment, chemical binding techniques are used to immobilize the first mip to the metal-containing layer surface. The presence of an analyte which is a second mip in a liquid sample is detected by wetting the metal-containing layer steps upon which the first mip is immobilized with the liquid sample. Any second mip/analyte present in the liquid sample is captured by the first mip immobilized upon the metal-containing layer steps. This immunological binding followed by an aminosilane which can be attached to Si-OH and the proteins to the amino group of the silane between first and second mips results in an increase in the metal-containing layer step thickness which is visually manifested by a change in the observed color of that step from a perspective directly above the metal-containing layer step. Semi-quantitative and quantitative analysis of the amount of analyte present in the liquid sample is made possible by comparison of step colors on the unknown device with step colors on a standard device calibrated for known concentrations.

The optical immunosensing device can be fabricated by spin-coating iron phosphate (and optionally, aluminum phosphate, silicon dioxide, or mixtures thereof) in solution onto the surface of a silicon wafer. Then, phosphoric acid is applied to the metal-containing layer for various exposure times to etch a series of metal-containing layer steps of varying thickness. The first mip is then immobilized on the surface of the metal-containing layer steps, either by chemical (covalent) or physical means (adsorption), chemical techniques being preferred.

Optimum sensitivity and performance of the optical immunosensing device is obtained when the reflectivity at the interface between the metal coating and silicon wafer substrate is matched with the reflectivity of the metal-containing layer at the metal-air interface. Further enhancement is possible if the index of refraction of the metal-containing layer steps is matched closely to the index of refraction of the first bound mip.

DETAILED DESCRIPTION OF THE INVENTION

Figure 1:
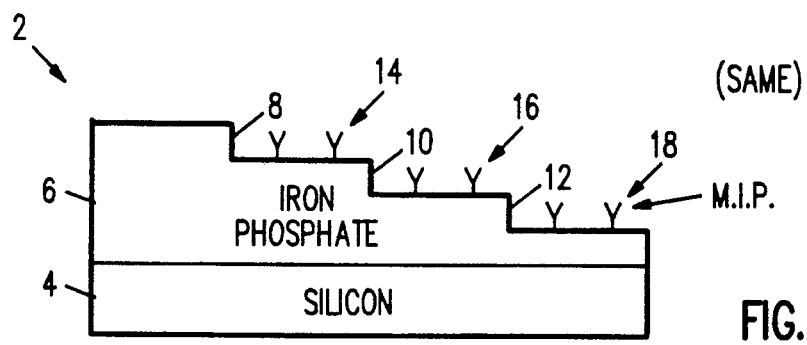
FIG. 1 is a plan view of the layers of the optical immunosensing device of the present invention.

Before describing the optical immunosensing device itself, it is first necessary to define the components of the immunological systems in which the device can be used. While the terms antigen and antibody are commonly used in the scientific literature, it is necessary for present purposes to become more accurate and to account for systems in which haptens are subject to immunological binding and detection. It is considered to be within the scope of this invention that if the target analyte of the immunosensing device is an antibody, the immobilized capture phase will actually be an antibody to an antibody. The various types of immunological systems in which the present invention can be used are described in rigorous detail below.

Here, we adopt a series of definitions for purposes of describing the invention accurately with a view towards the various and diverse systems in which it can be used as an immunoassay.

Analyte is used throughout this specification to refer to the compound or composition to be detected and measured, which is a mip and may be a ligand, which is mono- or polyepitopic, that is, having one or plurality of determinant sites, haptenic and antigenic; a single compound or plurality of compounds which share at least one common epitopic or determinant site; or a receptor.

Member of an immunological pair (mip) is used to acknowledge the complimentarity of antigens-antibodies, haptens-antibodies, even antibodies-antibodies. An immunological pair consists of two different molecules wherein one of the molecules has an area on its surface or in a cavity which specifically binds to a particular spatial and polar organization of the other molecule in the pair. The members of the immunological pair are referred to as ligand and receptor (anti-ligand). The term "member" of the immunological pair refers to one "member" of this binding pair.

Ligand—any organic compound for which a receptor exists or can be prepared.

Receptor (antiligand)—any macromolecular compound or composition capable of recognizing (having an enhanced binding affinity to) a particular spatial or determinant site. Illustrative receptors include naturally occurring receptors, e.g., thyroxine binding globulin, antibodies, enzymes, Fab fragments, lectins, and the like. The term antibody is employed in this case as illustrative of and to more generally denote receptor.

Antireceptor—in some situations, a receptor can serve a dual function of binding to a ligand and serving as a ligand to a receptor (antireceptor), such that the ligand and the antireceptor, which cannot bind directly to each other, are joined by the receptor to provide for an immunological linkage. Antireceptors may frequently be antibodies, protein A, rheumatoid factor, Clq. or the like.

The detection zone is used to refer to the metal-containing layer or iron phosphate steps of the optical immunosensing device upon which a first mip is immobilized and which will be used to detect the presence (and amount) of analyte present in a liquid sample. The detection zone may consist of a single step, and may also be a plurality of steps. The first mip may be chemically bound to the stepped layer surface, or it may be physically adsorbed.

Wetting is intended to cover at least two methods of applying the liquid sample containing the analyte to the detection zone, i.e., the area in which the first mip has been immobilized on the surface of the step: (1) the liquid sample may be applied to the detection zone dropwise, or continuously, through a dropper pipette, or closed container surrounding the detection zone or (2) the entire immunosensing device itself, or just the detection zone alone, may be immersed in the liquid sample to wet the detection zone.

Liquid sample is defined broadly to refer to physiological fluids such as urine, blood—whole serum or plasma, cerebral spinal fluid, ocular lens liquid and saliva; solutions made from swabbing surfaces or to a solution of such bodily fluids and swabs, or to a solution of a solid protein dissolved in a liquid. The essential characteristic of the liquid sample is that the liquid sample must be able to contain the analyte in solution and to wet the detection zone. Otherwise, there can be no immunological binding between mips.

There is a functional aspect of the immunological system which must be accounted for in the design of the optical immunosensing device: there must be a reasonable immunological binding affinity between the selected mips, i.e., the target analyte and the solid-immobilized capture phase. The immunological reaction kinetics must be carefully studied to ensure that the immunological binding between the mips will take place in a reasonable short period of time, that the immunological bond that is formed is sufficiently strong to withstand the flushing action of excess liquid and that the bond is of sufficient duration in time to enable visual observations of the result. While the definition of the exact parameters for each of these kinetic considerations is outside the scope of the present invention, the ordinary artisan will be able to select mips which can optimize the instant invention without undue experimentation.

The concentration of the analyte which may be assayed with the optical immunosensing device will generally vary from about $10^{-4}$ to $10^{-15}$, more usually from about $10^{-6}$ to $10^{-13}$ M. Considerations such as whether the assay is qualitative, semi-quantitative or quantitative and the particular detection technique will normally determine the sensitivity of the device.

The fundamental components of the device 2 are shown in FIG. 1. Onto the smooth surface of a substrate 4, a transparent thin film 6 is deposited. This film 6 is etched to obtain first step 8, second step 10 and third step 12. Then, mip is immobilized upon step surfaces 8, 10 and 12 either by chemical bonds or by physical means, to obtain first mip on first step 14, first mip on second step 16 and first mip on third step 18.

The selection of the substrate 4 is dependent upon the intensity of the light reflected at the interface between the substrate 4 and the film 6, and upon the intensity of the light reflected at the film 6—air interface. Reflectivity at a particular interface is large when the differences in indices of refraction (n) of the two materials forming the interface are large. Thus, $n_{sub} >> n_{film} >> n_{air}$ is desired. Since $n_{film}$ is always much larger than $n_{air}$, this condition is easily satisfied. $n_{sub} >> n_{film}$ can be satisfied by the use of metallic substrates (e.g. $n_{cr} = 3.0$), but if the substrate is too shiny, the light reflected at the film-substrate interface becomes more intense than the light reflected at the film-air interface, thus obscuring the signal, i.e., interference color change. This makes silicon and titanium desirable substrate materials. On the other end of the spectrum, substrate materials with low indices of refraction provide a weak reflection of light at the substrate-film interface. This also leads to a weak signal. For example, glass shows weak interference colors when it is coated with dielectrics. In particular, a glass plate shows practically no interference colors when it is coated with $SiO_2$ because glass has $n_{sub} = 1.51$ which is very close to that of $SiO_2$ ($n_{sub} = 1.47$).

Physical coating techniques and chemical coating techniques can be used to apply a transparent thin film 6 to the substrate 4. Vacuum deposition may be used. Spin-coating is very simple and effective if it can be used with the desired film material. For example, $TiO_2$, $SiO_2$ and $FePO_4$ can be spin-coated from appropriate solutions even though the mechanisms of film-forming are different. $TiO_2$ and $SiO_2$, and mixtures thereof, are formed by a sol-gel process, whereas $FePO_4$ is not. One chemical method which can be used to apply the film is dip-coating. $TiO_2$, $SiO_2$ and their mixtures, are materials which are suitable for this method. $FePO_4$ however, cannot be applied via dip-coating because the film lifted out of solution is attacked by the solvent vaporized and condensed on the film.

Steps in the thin film 6 can be made either during the coating process, or after the film has been coated on the substrate. The procedure selected is a function of the film material and how this material has been coated on the substrate. Since $TiO_2$-$SiO_2$ mixtures can be applied to the substrate via the dip-coating method, steps can be made during the dip-coating process. Many materials, which can be applied via vacuum deposition, can be formed into steps during the deposition procedure by moving an appropriate shutter stepwise.

Figure 2:
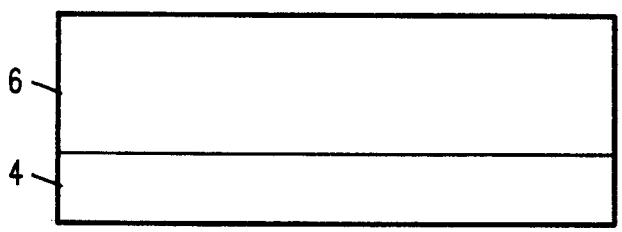
FIG. 2 is a plan view during fabrication of the optical immunosensing device, after an iron phosphate layer is deposited upon the silicon substrate, but prior to any etching with phosphoric acid.
Figure 3:
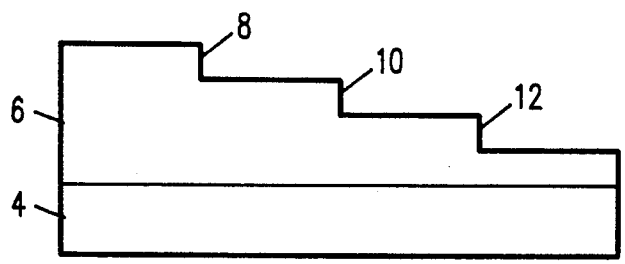
FIG. 3 is a plan view during fabrication of the optical immunosensing device, showing the steps of varying thickness etched into an iron phosphate layer with phosphoric acid.

In one of the preferred embodiments using iron phosphate, step-formation takes place after the entire film 6 has been deposited on the silicon wafer substrate 4. This is most easily explained with reference to FIGS. 2 and 3. After the iron phosphate layer has been applied to the silicon wafer substrate 4, the iron phosphate film 6 is then etched with phosphoric acid in order to obtain first step 8, second step 10 and third step 12. The steps 8, 10 and 12 are carefully formed by using a mask which exposes the desired surface area to the etching acid, while shielding all other surfaces. The depth of the etch is controlled by the amount of time the phosphoric acid is permitted to act upon the iron phosphate surface. Any number of steps can be formed in this way. The most significant limitation on the size and number of steps is that one visually observes the result of the assay from a perspective directly above the step surfaces.

Figure 4A:
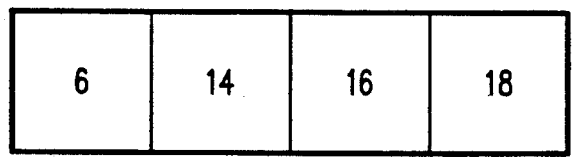
FIG. 4 is a top plan view of the colors visible on various iron phosphate steps, before and after exposure to a liquid sample containing the target analyte.
Figure 4B:
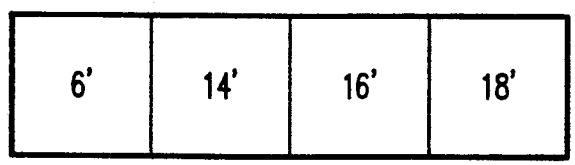

After the steps have been formed in the iron phosphate layer 6, mip is immobilized upon the step surfaces to obtain first mip on first step 14, first mip on second step 16 and first mip on third step 18, as shown in FIGS. 1 and 4. The protein can be immobilized by chemical (covalent) binding, or by physical methods such as adsorption. We have found chemical binding to be substantially more suited to the desired immobilization. In either case, the protein must be immobilized on the iron phosphate step surface so that it will not be released into the liquid sample when the detection zone is wetted with the liquid sample.

Before antibody can be immobilized on the surface of the thin film by chemical means, the appropriate functional groups need to be present on the surface of the film. Untreated iron phosphate film does not have the necessary surface functional groups. Thus, in our preferred embodiment, the surface of the iron phosphate film is treated with $TiO_2$ or $SiO_2$ to obtain hydroxyl groups on the surface of the iron phosphate film. Then, we use a cross-linking agent, amino silane, and a bifunctional agent like glutaraldehyde to immobilize the antibody on the surface of the film. The antibody should be dissolved in a buffer solution to prevent the protein from denaturing. This and similar techniques are well known in the literature. See, e.g., Weetal, *Immobilized Enzymes, Antigens, Antibodies and Peptides*, Published by Marcel Dekker, Inc., N.Y., N.Y., 1975.

Other protein immobilization techniques (both physical and chemical) are considered to be within the scope of this invention. When these other techniques are used, two important considerations are the stability of the protein immobilization to the film surface so that quantitative results may be obtained when the detection zone is wetted with the liquid sample; and, the geometric configuration of the immobilized protein to insure that the epitopic sites relevant to the immunoassay are actually exposed to the target analyte present in the liquid sample. Some of these immobilization techniques involve the covalent coupling of proteins to the thin film layer. See Weetal, *Immobilized Enzymes, Antigens, Antibodies and Peptides*, Published by Marcel Dekker, Inc., N.Y., N.Y. (1975), the relevant portions of which are incorporated by reference. Other immobilization methods involve physical processes such as adsorption.

We now turn to a description of the fabrication of the presently preferred embodiment. In summary, there are seven process steps. In the first step, we obtain a clean silicon wafer, or other suitable substrate. Second, we apply an undercoating adhesion layer if it is necessary. Then, iron phosphate is coated onto the substrate in a single layer, which is followed by etching to obtain iron phosphate steps of varying thickness. In the fifth step, a top oxide layer of either $TiO_2$ or $SiO_2$ is provided to give surface hydroxyl groups capable of participating in the mip-immobilization reaction. This top oxide layer surface is then treated with a chemical cross-linking agent, if necessary. In the final step, antibody or protein is applied to the top oxide layer to obtain the immunoreactive surface required for sensing, i.e. immobilized first mip.

When a silicon wafer is used, its surface is normally clean enough so that no further surface cleaning is required prior to the iron phosphate film coating procedures. When micro glass slides are used as the coating substrate, they are dirtier than the silicon wafers, and a two step cleaning process is employed prior to any iron phosphate coating. Water-soluble materials are removed from the glass surface in a water-wash step, followed by an acetone/isopropanol wash step to remove organic contamination from the glass surface.

In determining the need for an undercoating adhesion layer between the substrate and the iron phosphate layer, it is necessary to examine each class of substrates. Silicon wafers can be obtained with or without $SiO_2$ top layers which can be thermally grown. Silicon wafers without $SiO_2$ will require an undercoating adhesion layer. Micro glass slides do not need an undercoating adhesion layer. Plastic strips can also be used as substrates for the optical immunosensor. When we use such plastic strips, we coat the plastic strip surface with a moderately shiny material, e.g., titanium metal. Titanium metal-coated strips require an undercoating adhesion layer.

In our preferred embodiment, we use Ti-isopropoxide solution (0.5 ml in 100 ml isopropanol) to obtain an undercoating film of ~100 Å Ti(OH). or $TiO_2$ films. A more concentrated solution produces thicker films (2000 Å) of inconsistent quality. When the undercoating is too thin, there is poor adhesion. This poor adhesion occurred when a solution of 0.25 ml Ti-isopropoxide in 100 ml isopropanol was used. It is possible to use silicon dioxide films as the undercoating adhesion films. "Liqui-coat" supplied by Merck is a suitable, commercially available film. Other sol-gel films are available, and can be easily identified in the trade journal *Thin Solid Films*.

When iron phosphate solutions are used to coat the substrate, special safety precautions must be taken in the laboratory. Iron phosphate solution may explode when it is stored in sealed bottles as a result of bubble formation. Loose sealing of vessels containing iron phosphate solutions is recommended, particularly just after the solutions are prepared.

In coating iron phosphate onto a substrate, we use a spin coating technique. Iron phosphate is obtained by mixing $FeCl_3$(1M) and $H_3PO_4$ (1M) in methanol. $Fe(NO_3)_3$ can be dissolved in methanol and combined with or substituted for, the iron chloride. When the nitrate form is used, the resulting film is almost colorless white; films using $FeCl_3$ are yellow. When the subsequent etching step can be performed quickly, we recommend a solution of $Fe:PO_4=1:1$. When slower etching equipment is used, we recommend 1:1.5 or 1:2. Films made from $Fe(NO_3)_3$, 1:1.5 or 1:2, become white after etching. On the contrary, films made from $FeCl_3$, 1:1.5 or 1:2, are very good.

After the iron phosphate layer has been applied, we treat the iron phosphate surface to obtain surface hydroxyl groups which are useful in covalently binding the proteins (mips) to the iron phosphate surface. Ti-isopropoxide solution works well for this "top-coating," even in dilute solutions (0.25 ml Ti-isopropoxide in 100 ml isopropanol). Once the $Ti(OH)_4$ film is present, we heat the film to $-300°$ C. to convert the $Ti(OH)_4$ to $TiO_2$. At temperatures lower than 300° C. (e.g., 200° C.), water is driven from the $Ti(OH)_4$ film and it becomes tacky which may be adequate for the protein (mip) immobilization. We have not yet undertaken systematic studies to evaluate the performance of detection zones fabricated in each of these two ways. We do understand, however, that lower temperatures are preferable for other reasons because iron phosphate can deteriorate from heating at temperatures in excess of 300° C.

We turn now to the different analyte systems to which this invention can be applied. The ligand analytes of this invention are characterized by being monoepitopic or polyepitopic. The polyepitopic ligand analytes will normally be poly (amino acids) i.e. polypeptides and proteins, polysaccharides, nucleic acids, and combinations thereof. Such combinations of assemblages include bacteria, viruses, chromosomes, genes, mitochondria, nuclei, cell membranes, and the like.

For the most part, the polyepitopic ligand analytes employed in the subject invention will have a molecular weight of at least about 5,000, more usually at least about 10,000. In the poly (amino acid) category, the poly (amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

A wide variety of proteins may be considered: the family of proteins having similar structural features; proteins having particular biological functions, proteins related to specific microorganisms; particularly disease causing microorganisms; etc.

The following are classes of proteins related by structure:

protamines
histones
albumins
globulins
scleroproteins
phosphoproteins
mucoproteins
chromoproteins
lipoproteins
nucleoproteins
glycoproteins
proteoglycans
unclassified proteins, e.g. somatotropin,
prolactin, insulin, pepsin
A number of proteins found in the human plasma are important clinically and include:

Prealbumin
Albumin
$\alpha_1$-Lipoprotein
$\alpha_1$-Acid glycoprotein
$\alpha_1$-Antitrypsin
$\alpha_1$-Glycoprotein
Transcortin
4.6S-Postalbumin
Tryptophan-poor
$\alpha_1$-Glycoprotein
$\alpha_1\chi$-Glycoprotein
Thyroxin-binding globulin
Inter-$\alpha$-trypsin-inhibitor
Gc-globulin
(Gc 1-1)
(Gc 2-1)
(Gc 2-2)
Haptoglobin
(Hp 1-1)
(Hp 2-1)
(Hp 2-2)
Ceruloplasmin
Cholinesterase
$\alpha_2$-Lipoprotein(s)
Myoglobin
C-Reactive Protein
$\alpha_2$-Macroglobulin
$\alpha_2$-HS-glycoprotein
Zn-$\alpha_2$-glycoprotein
$\alpha_2$-Neuramino-glycoprotein
Erythropoietin
$\beta$-lipoprotein
Transferrin -continued Hemopexin
Fibrinogen
Plasminogen
$\beta_2$-glycoprotein I
$\beta_2$-glycoprotein II
Immunoglobulin G
(IgG) or $\gamma$G-globulin
Mol. formula:
$\gamma_2\kappa_2$ or $\gamma_2\lambda_2$
Immunoglobulin A (IgA)
or $\gamma$A-globulin
Mol. formula:
$(\alpha_2\kappa_2)^n$ or $(\alpha_2\lambda_2)^n$
Immunoglobulin M
(IgM) or $\gamma$M-globulin
Mol. formula:
$(\mu_2\kappa_2)^5$ or $(\mu_2\lambda_2)^5$
(Immunoglobulin D(IgD)
or $\gamma$D-Globulin ($\gamma$D)
Mol. formula:
$(\delta_2\kappa_2)$ or $(\delta_2\lambda_2)$
Immunoglobulin E (IgE)
or $\gamma$E-Globulin ($\gamma$E)
Mol. formula:
$(\epsilon_2\kappa_2)$ or $(\epsilon_2\lambda_2)$
Free $\kappa$ and $\lambda$ light chains Complement factors:

C'1
    C'1q
    C'1r
    C'1s
C'2
C'3
    $\beta_1$A
    $\alpha_2$D
C'4
C'5
C'6
C'7
C'8
C'9

Important blood clotting factors include:

Blood Clotting Factors

| International designation | Name |
|---|---|
| I | Fibrinogen |
| II | Prothrombin |
| IIa | Thrombin |
| III | Tissue thromboplastin |
| V and VI | Proaccelerin accelerator globulin |
| VII | Proconvertin |
| VIII | Antihemophilic globulin (AHG) |
| IX | Christmas factor, plasma thromboplastin component (PTC) |
| X | Stuart-Prower factor, autoprothrombin III |
| XI | Plasma thromboplastin antecedent (PTA) |
| XII | Hagemann factor |
| XIII | Fibrin-stabilizing factor |

Important protein hormones include:

Peptide and Protein Hormones

Parathyroid hormone
(parathromone)
Thyrocalcitonin
Insulin
Glucagon
Relaxin
Erythropoietin
Melanotropin
(melanocyte-stimulating hormone; intermedin)
Somatotropin
(growth hormone)
Corticotropin
(adrenocorticotropic hormone)
Thyrotropin -continued Follicle-stimulating hormone
Luteinizing hormone
(interstitial cell-stimulating hormone)
Luteomammotropic hormone
(luteotropin, prolactin)
Gonadotropin
(chorionic gonadotropin)

Tissue Hormones

Secretin
Gastrin
Angiotensin I and II
Bradykinin
Human placental lactogen

Peptide Hormones from the Neurohypophysis

Oxytocin
Vasopressin

Releasing factors

CRF, LRF, TRF, Somatotropin-RF, GRF, FSH-RF, PIF, MIF

Other polymeric materials of interest are mucopolysaccharides and polysaccharides. Illustrative antigenic polysaccharides derived from microorganisms are as follows:

| Species of Microorganisms | Hemosensitin Found in |
|---|---|
| *Streptococcus pyogenes* | Polysaccharide |
| *Dislococcus pneumoniae* | Polysaccharide |
| *Neisseria meningitidis* | Polysaccharide |
| *Neisseria gonorrheae* | Polysaccharide |
| *Corynebacterium diphtheriae* | Polysaccharide |
| *Actinobacillus whitemori* | |
| *Francisella tularensis* | Lipopolysaccharide |
| *Pasteurella pestis* | Polysaccharide |
| *Pasteurella multocida* | Capsular antigen |
| *Brucella abortus* | Crude extract |
| *Haemophilus influenzae* | Polysaccharide |
| *Haemophilus pertussis* | Crude |
| *Treponema reiteri* | Polysaccharide |
| *Veillonella* | Lipopolysaccharide |
| *Erysipelothrix* | Polysaccharide |
| *Listeria monocytogenes* | Polysaccharide |
| *Chromobacterium* | Lipopolysaccharide |
| *Mycobacterium tuberculosis* | Saline extract of 90% phenol extracted mycobacteria and polysaccharide fraction of cells and tuberculin |
| *Klebsiella aerogenes* | Polysaccharide |
| *Klebsiella cloacae* | Polysaccharide |
| *Salmonella typhosa* | Lipopolysaccharide Polysaccharide |
| *Salmonella typhi-murium* | Polysaccharide |
| *Salmonella derby* | |
| *Salmonella pullorum* | |
| *Shigella dysenteriae* | Polysaccharide |
| *Shigella sonnei* | Crude, Polysaccharide |
| Rickettsiae | Crude extract |
| *Candida albicans* | Polysaccharide |
| *Entamoeba histolytica* | Crude extract |

The microorganisms which are assayed may be intact, lysed, ground or otherwise fragmented, and the resulting composition or portion, e.g. by extraction, assayed. Microorganisms of interest include:

Corynebacteria
  *Corynebacterium dipheriae*
Pneumococci
  *Diplococcus pneumoniae*
Streptococci
  *Streptococcus pyogenes*
  *Streptococcus salivarus*
Staphylococci
  *Staphylococcus aureus*
  *Staphylococcus albus*
Neisseriae
  *Neisseria meningitidis*
  *Neisseria gonorrheae*

-continued

Enterobacteriaciae

Escherichia coli  ⎫
Aerobacter aerogenes  ⎬ The coliform bacteria
Klebsiella pneumoniae ⎭

Salmonella typhosa  ⎫
Salmonella choleraesuis  ⎬ The Salmonellae
Salmonella typhimurium ⎭

Shigella dysenteriae  ⎫
Shigella schmitzii
Shigella arabinotarda
Shigella flexneri  ⎬ The Shigellae
Shigella boydii
Shigella sonnei ⎭

Other enteric bacilli

Proteus vulgaris  ⎫
Proteus mirabilis
Proteus morgani  ⎬ Proteus species
Pseudomonas aeruginosa
Alcaligenes faecalis ⎭

Vibrio cholerae
Hemophilus-Pordetella group
Hemophilus influenzae.
H. ducreyi
H. hemophilus
H. aegypticus
H. parainfluenzae
Bordetella pertussis Pasteurellae Pasteurella pestis
Pasteurella tulareusis Brucellae Brucella melitensis
Brucella abortus
Brucella suis Aerobic Spore-forming Bacilli Bacillus anthracis
Bacillus subtilis
Bacillus megaterium
Bacillus cereus Anaerobic Spore-forming Bacilli Clostridium botulinum
Clostridium tetani
Clostridium perfringens
Clostridium novyi
Clostridium septicum
Clostridium histolyticum
Clostridium tertium
Clostridium bifermentans
Clostridium sporogenes Mycobacteria Mycobacterium tuberculosis hominis
Mycobacterium bovis
Mycobacterium avium
Mycobacterium leprae
Mycobacterium paratuberculosis Actinomycetes (fungus-like bacteria)

Actinomyces israelii
Actinomyces bovis
Antinomyces naeslundii
Nocardia asteroides
Nocardia brasilienis The Spirochetes Treponema pallidum
Treponema pertenue
Treponema carateum
Borrelia recurrentis
Leptospira icterohemorrhagiae
Leptospira canicola
Spirillum minus
Streptobacillus moniliformis
Mycoplasmas
Mycoplasma pneumoniae Other pathogens Listeria monocytogenes
Erysipelothrix rhusiopathiae
Streptobacillus moniliformis
Donvania granulomatis
Bartonella bactillformi Rickettsiae (bacteria-like parasites)

-continued

Rickettsia prowazekii
Rickettsia mooseri
Rickettsia rickettsii
Rickettsia conori
Rickettsia australis
Rickettsia sibiricus
Rickettsia akari
Rickettsia tsutsugamushi
Rickettsia burnetii
Rickettsia quintana
Chlamydia (unclassifiable parasites bacteria/viral)
Chlamydia agents (naming uncertain)

Fungi

Cryptococcus neoformans
Blastomyces dermatidis
Histoplasma capsulatum
Coccidioides immitis
Paracoccidioides brasiliensis
Candida albicans
Aspergillus fumigatus
Mucor corymbifer (Absidia corymbifera)
Rhizopus oryzae  ⎫
Rhizopus arrhizus  ⎬ Phycomycetes
Rhizopus nigricans ⎭
Sporotrichum schenkii
Fonsecaea pedrosoi
Fonsecaea compacta
Fonsecaea dermatidis
Cladosporium carrionii
Phialophora verrucosa
Aspergillus nidulans
Madurella mycetomi
Madurella grisea
Allescheria boydii
Phialosphora jeanselmei
Microsporum gypseum
Trichophyton mentagrophytes
keratinomyces ajelloi
Microsporum canis
Trichophyton rubrum
Microsporum andouini Viruses
Adenoviruses Herpes Viruses Herpes simplex
Varicella (Chicken pox)
Herpes Zoster (Shingles)
Virus B
Cytomegalovirus Pox Viruses Variola (smallpox)
Vaccinia
Poxvirus bovis
Paravaccinia
Molluscum contagiosum Picornaviruses Poliovirus
Coxsackievirus
Echoviruses
Rhinoviruses Myxoviruses Influenza (A, B, and C)
Parainfluenza (1–4)
Mumps Virus
New Castle Disease Virus
Measles Virus
Rinderpest Virus
Canine Distemper Virus
Respiratory Syncytial Virus
Rubella Virus Arboviruses Eastern Equine Eucephalitis Virus
Western Equine Eucephalitis Virus
Sindbis Virus
Chikugunya Virus
Senliki Forest Virus
Mayora Virus
St. Louis Encephalitis Virus
California Encephalitis Virus
Colorado Tick Fever Virus
Yellow Fever Virus -continued Dengue Virus
Reoviruses
Reovirus Types 1-3
Hepatitis
Hepatitis A Virus
Hepatitis B Virus
Tumor Viruses
Rauscher Leukemia Virus
Gross Virus
Maloney Leukemia Virus The monoepitopic ligand analytes will generally be from about 100 to 2,000 molecular weight, more usually from 125 to 1,000 molecular weight. The analytes of interest include drugs, metabolites, pesticides, pollutants, and the like. Included are the alkaloids: morphine alkaloids, which includes morphine, codeine, heroin, dextromethorphan, their derivatives and metabolites; cocaine alkaloids, which includes cocaine and benzoyl ecgonine, their derivatives and metabolites; ergot alkaloids, which includes the diethylamide of lysergic acid; steroid alkaloids; iminazoyl alkaloids; quinazoline alkaloids, isoquinoline alkaloids; quinoline alkaloids; which includes quinine and quinidine; diterpene alkaloids, their derivatives and metabolites.

The next group of drugs includes steroids which includes the estrogens, gestrogens, androgens, adrenocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

The next group of drugs is lactams having from 5 to 6 annular members, which include the barbiturates, e.g. phenobarbital and secobarbital, diphenylhydantoin, primidone, ethosuximide, and their metabolites.

The next group of drugs is aminoalkylbenzenes with alkyl of from 2 to 3 carbon atoms, which includes the amphetamines, catecholamines, which includes ephedrine, L-dopa, epinephrine, narceine, papaverine, and their metabolites.

The next group of drugs is benzheterocyclics which include oxazepam, chlorpromazine, tegretol, imipramine, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs includes the vitamins such as A, B, e.g. $B_{12}$, C, D, E and K, folic acid, thiamine.

The next group of drugs is prostaglandins, which differ by the degree and sites of hydroxylation and unsaturation.

The next group of drugs is antibiotics, which include penicillin, chloromycetin, actinomycetin, tetracycline, terramycin, their metabolites and derivatives.

The next group of drugs is the nucleosides and nucleotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, amitriptyline, nortriptyline, lidocaine, procaineamide, acetylprocaineamide, propranolol, griseofulvin, valproic acid, butyrophenones, antihistamines, anticholinergic drugs, such as atropine, their metabolites and derivatives.

The next group of compounds is amino acids and small peptides which include polyiodothyronines e.g. thyroxine, and triiodothyronine, oxytocin, ACTH, angiotensin, met-and lu-enkephalin their metabolites and derivatives.

Metabolites related to diseased states include spermine, galactose, phenylpyruvic acid, and porphyrin Type 1.

The next group of drugs is aminoglycosides, such as gentamicin, kanamycin, tobramycin, and amikacin.

Among pesticides of interest are polyhalogenated biphenyls, phosphate esters, thiophosphates, carbamates, polyhalogenated sulfenamides, their metabolites and derivatives.

For receptor analytes, the molecular weights will generally range from 10,000 to $2 \times 10^6$, more usually from 10,000 to $10^6$. For immunoglobulins, IgA, IgG, IgE and IgM, the molecular weights will generally vary from about 160,000 to about $10^6$. Enzymes will normally range from about 10,000 to 6,000,000 in molecular weight. Natural receptors vary widely, generally being at least about 25,000 molecular weight and may be $10^6$ or higher molecular weight, including such materials as avidin, thyroxine binding globulin, thyroxine binding prealbumin, transcortin, etc.

The optical immunosensor of the present invention can be used qualitatively, semi-quantitatively or quantitatively. When the device is used semi-quantitatively, the user can be directed that certain color changes correspond to particular concentration levels of the target analyte. When the device is utilized for quantitative measurement, a reference device is employed with the sensor device under the same liquid sample conditions. For example, a single wafer can be marked with two channels, one the testing/sensor channel, and the other the reference channel. If the concentration of protein on the reference channel is known (i.e., concentration of protein is proportional to thickness is related to color) then the sensor channel can be quantified by reference to the color changes as compared to the reference channel, which will not undergo any color change upon exposure to the liquid sample.

WORKING EXAMPLES

Example 1

Using a silicon wafer as a substrate, steps of $FePO_4$ were made according to the following procedure:

An iron phosphate solution was obtained by mixing $FeCl_3$ (1M) and $H_3PO_4$ (1M) in methanol. This solution was then spin coated onto a silicon wafer at 5000 RPM and ambient temperatures. The resulting iron phosphate layer was then etched with $H_3PO_4$. Steps of varying iron phosphate thickness were obtained by dipping the coated wafer into the acid at different lengths and for different times. Interference colors with sharp contrast were obtained between steps.

Example 2

A silicon substrate with iron phosphate steps was left in contact with a 10% solution of albumin overnight. When the steps were removed from the albumin solution and the solution was allowed to evaporate from the surface, essentially albumin dried on the steps resulting in a thickness change. This thickness change was manifested by a shift in colors of several steps, indicating that thickness changes can be monitored by this procedure. However, when the albumin was washed with a jet of water, most of the albumin was washed away as seen by only a faint change in color. This was interpreted to mean that the albumin was probably not adsorbed on the $FePO_4$ surface.

An iron phosphate solution was obtained by mixing $FeCl_3$ (1M) and $H_3PO_4$ (1M) in methanol. This solution was then spin coated onto a silicon wafer at 5000 RPM and ambient temperatures. The resulting iron phosphate layer was then etched with $H_3PO_4$. Steps of varying iron phosphate thickness were obtained by dipping the coated wafer into the acid at different lengths and for different times. Interference colors with sharp contrast were obtained between steps.

We claim:

1. An apparatus for visually detecting the presence of an analyte which is a member of an immunological pair (mip) in a liquid sample which comprises:
    a) a silicon substrate;
    b) an iron phosphate layer, coated onto said silicon substrate and etched to form discrete steps of varying iron phosphate thickness; and,
    c) a first mip immobilized upon the surface of said iron phosphate steps to form a detection zone whereby the presence of the analyte which is a second mip in the liquid sample is detected by wetting the detection zone with the liquid sample, and observing any color change in the detection zone resulting from the increased thickness of the iron phosphate steps caused by the binding of the second mip to the first mip immobilized upon the iron phosphate steps in the detection zone.

2. The apparatus of claim 1 wherein said iron phosphate layer further comprises aluminum phosphate.

3. The apparatus of claim 1 wherein an undercoating adhesion layer is provided between the silicon substrate and the iron phosphate layer.

4. The apparatus of claim 1 wherein said first mip is immobilized upon the iron phosphate layer via chemical bonds.

5. An apparatus for visually detecting the presence of an analyte which is a member of an immunological pair (mip) in a liquid sample which comprises:
    a substrate having at least one flat surface for receiving a stepped layer;
    the stepped layer, coated onto said substrate with at least one step with flat surfaces parallel to the substrate flat surface wherein the reflectivity at a substrate-stepped layer interface is substantially the same as the reflectivity at the interface between the stepped layer and air; and,
    a detection zone in which a first mip is immobilized upon step surfaces of the stepped layer, the index of refraction of said immobilized first mip being substantially similar to the index of refraction of said stepped layer, whereby the presence of the analyte which is a second mip in the liquid sample is detected by wetting the detection zone with the liquid sample, and observing any color change in the detection zone resulting from an increased thickness of the at least one step caused by binding of the second mip to the first mip immobilized upon the at least one step.

6. The apparatus of claim 5 wherein said substrate is silicon.

7. The apparatus of claim 5 wherein said stepped layer comprises iron phosphate.

8. The apparatus of claim 5 wherein said stepped layer comprises a mixture of iron phosphate and aluminum phosphate.

9. The apparatus of claim 5 wherein said at least one step with flat surface is obtained by controlled coating of the stepped layer material onto the substrate.

10. The apparatus of claim 5 wherein said at least one step with flat surface is obtained by etching the stepped layer material at precise conditions.

11. The apparatus of claim 5 wherein said first mip is immobilized in the detection zone via chemical bonds.

* * * * *